US00PP35308P2

(12) United States Plant Patent
Holtkamp

(10) Patent No.: US PP35,308 P2
(45) Date of Patent: Aug. 8, 2023

(54) ***PEPEROMIA* PLANT NAMED 'VERDANT FLAME'**

(50) Latin Name: *Peperomia polybotrya*
Varietal Denomination: Verdant Flame

(71) Applicant: Hermann Holtkamp Greenhouses, Inc., Nashville, TN (US)

(72) Inventor: Lawrence Holtkamp, Nashville, TN (US)

(73) Assignee: HERMANN HOLTKAMP GREENHOUSES, INC., Nashville, TN (US)

( * ) Notice: Subject to any disclaimer, the term of this patent is extended or adjusted under 35 U.S.C. 154(b) by 0 days.

(21) Appl. No.: 17/951,493

(22) Filed: Sep. 23, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

PUBLICATIONS

International Code of Nomenclature for Cultivated Plants, Ninth Edition, Published by ISHS Jun. 2016 (6 pages total).*

* cited by examiner

*Primary Examiner* — Susan McCormick Ewoldt
(74) *Attorney, Agent, or Firm* — Foley & Lardner LLP

(57) ABSTRACT

A new and distinct cultivar of *Peperomia* plant named 'Verdant Flame' particularly characterized by its variegated pale yellowish green foliage with irregular bands of medium green and grayish green in the center of the leaves. 'Verdant Flame' has varying amounts of medium green speckles between the veins, the amount of green speckles increases with the age of the leaves, has light green colored irregular bands in the center of the backside of the leaf blade. 'Verdant Flame' has wide and cordate leaves which produces thin elongated white flowers on long peduncles up to 30-50 cm and more in plant height; has erect plant habit, and is mildly drought tolerant with low need for water, and resistant to most diseases and pests.

5 Drawing Sheets

Latin name of the genus and species of the claimed plant: *Peperomia polybotrya.*

Variety denomination: 'VERDANT FLAME'.

BACKGROUND OF THE INVENTION

The present invention relates to a new and distinct cultivar of *Peperomia* plant botanically known as *Peperomia polybotrya* and hereinafter referred to by the cultivar name 'Verdant Flame'. 'Verdant Flame' originated from a discovery in our research facility. The cultivar 'Verdant Flame' was selected by the inventor Lawrence Holtkamp, in March 2019 in a controlled environment as a single plant within the progeny of regular 'Polybotrya' in an environmental controlled greenhouse area.

Asexual reproduction of the new cultivar 'Verdant Flame' first occurred by tip cuttings from stems in March 2019 in Nashville, Tenn. Since that time, multiple asexual reproductions have been conducted and under careful observation, the unique characteristics of the new cultivar have been uniform, stable and reproduced true to type in successive generations of asexual reproduction.

SUMMARY OF THE INVENTION

The following represents the distinguishing characteristics of the new *Peperomia* cultivar 'Verdant Flame'. These traits in combination distinguish 'Verdant Flame' as a new and distinct cultivar apart from other existing varieties of *Peperomia* known by the inventor.

1. *Peperomia* 'Verdant Flame' exhibits pale yellowish green leaves with irregular medium green and grayish green bands in the center.
2. *Peperomia* 'Verdant Flame' has varying amounts of small medium green speckles on the yellowish green areas in between the veins.
3. Mature leaves of *Peperomia* 'Verdant Flame' display significant amount of green speckles.
4. *Peperomia* 'Verdant Flame' exhibits heart-shaped leaves with a very fine purplish red line on the edge of the leaves.

The new variety 'Verdant Flame' presents an average of 7 or more leaves per plant when it reaches its maturity (between 3-4 months). The new variety has an erect growth habit, and the entire plant can reach a height of 30-50 cm and more. The leaves are slightly wide (8-10 cm average measured at the widest part of the mature leaf) and cordate with a soft waxy texture. As the plant matures, leaf sizes can increase to over 10-12 cm at the widest margin.

The plant is globe-shaped, wider at base and somewhat narrower at top.

The new variety is mildly drought tolerant, adapts to conditions of light and shade, and shows resistance to diseases and pests.

The closest comparison cultivars are *Peperomia polybotrya* (not patented). *Peperomia polybotrya* is distinguishable from 'Verdant Flame' by the following characteristics as described in Table 1.

TABLE 1

Comparison with Parental Varieties

| Characteristic | 'Verdant Flame' | *Peperomia polybotrya* (unpatented) |
|---|---|---|
| Plant Vigor | Slower growing due to variegated foliage lacking the amount of chlorophyll | medium |
| Color | Variegated foliage with varying amounts of green speckles | Plain green foliage |
| Shape | upright | upright |
| Texture of leaves | Smooth and waxy | Smooth and waxy |

Of the many commercial cultivars known to the present inventor, the most similar in comparison to the new *Peperomia* 'Verdant Flame' is the parent plain green *Peperomia polybotrya* (unpatented) in the characteristics described in Table 1. No other similar cultivar is known.

BRIEF DESCRIPTIONS OF THE PHOTOGRAPHS

The accompanying photographs illustrate the overall appearance of the new *Peperomia* cultivar 'Verdant Flame' showing the colors as true as is reasonably possible with colored reproductions of this type. Colors in the photographs may differ slightly from the color value cited in the detailed botanical description which accurately describe the color of 'Verdant Flame'.

BOTANICAL DESCRIPTION OF THE PLANT

Figure 1:
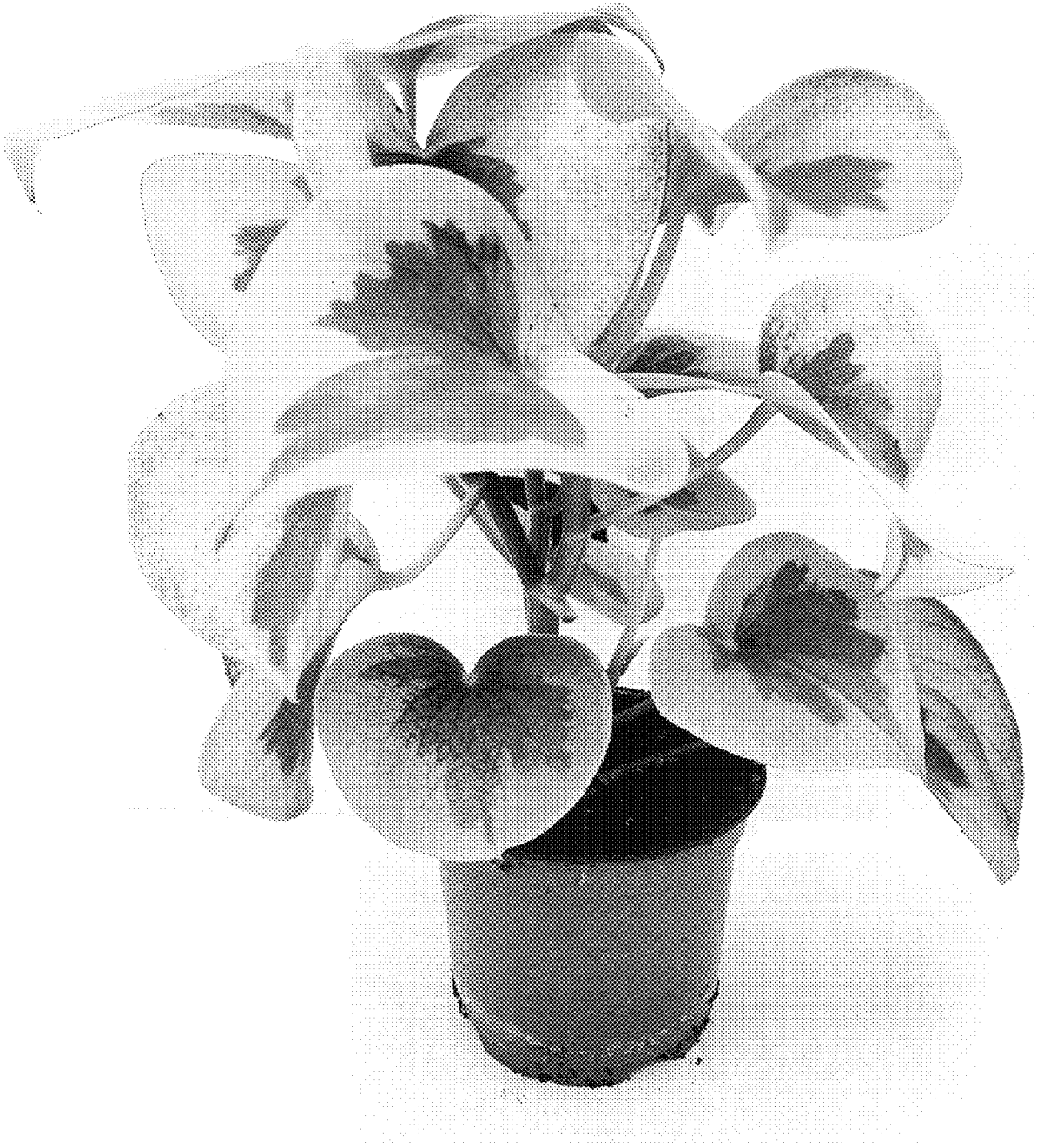
FIG. 1 shows a photo of the entire plant from the side.
Figure 2:
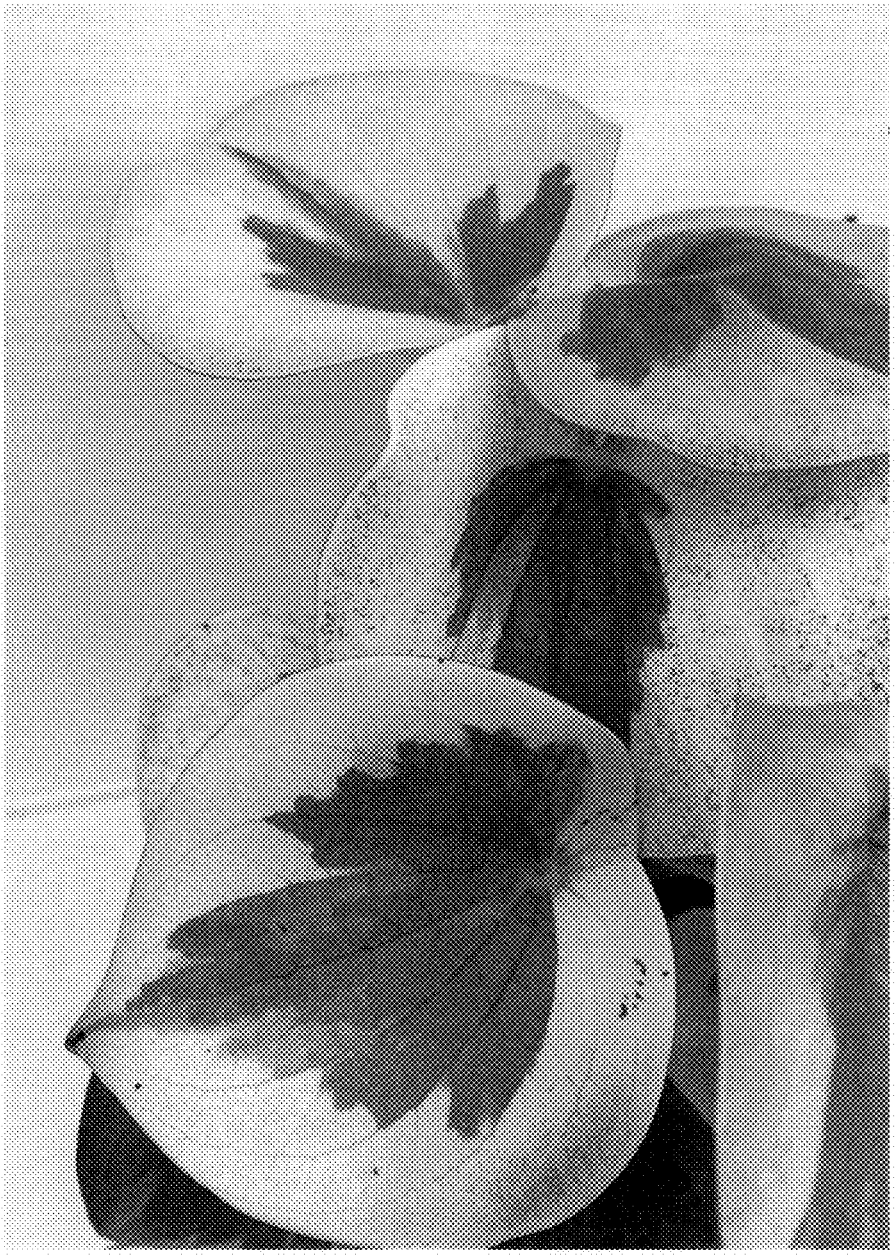
FIG. 2 shows a photo of the entire plant from the top.
Figure 3:
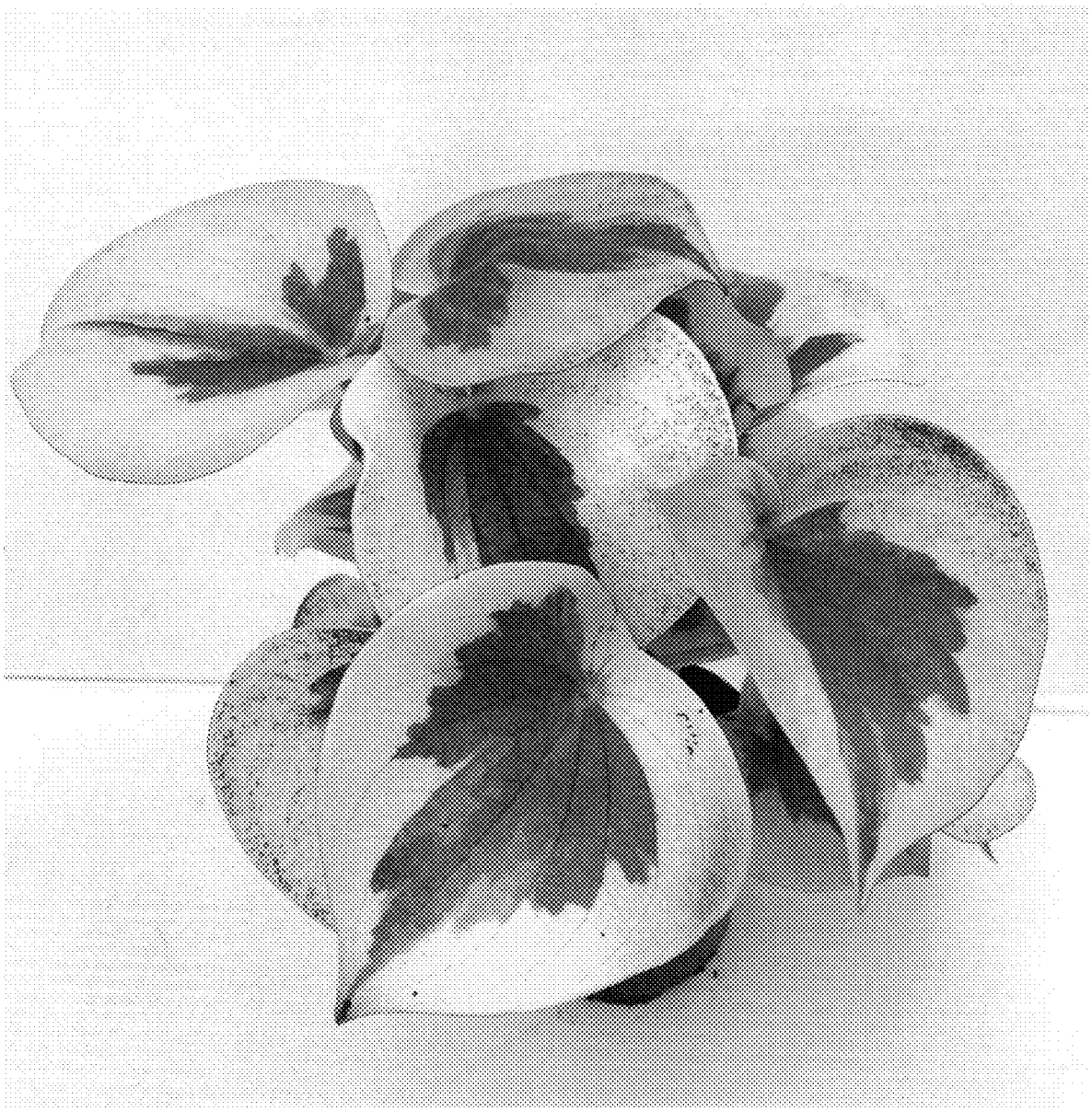
FIG. 3 shows a photo of young leaves.
Figure 4:
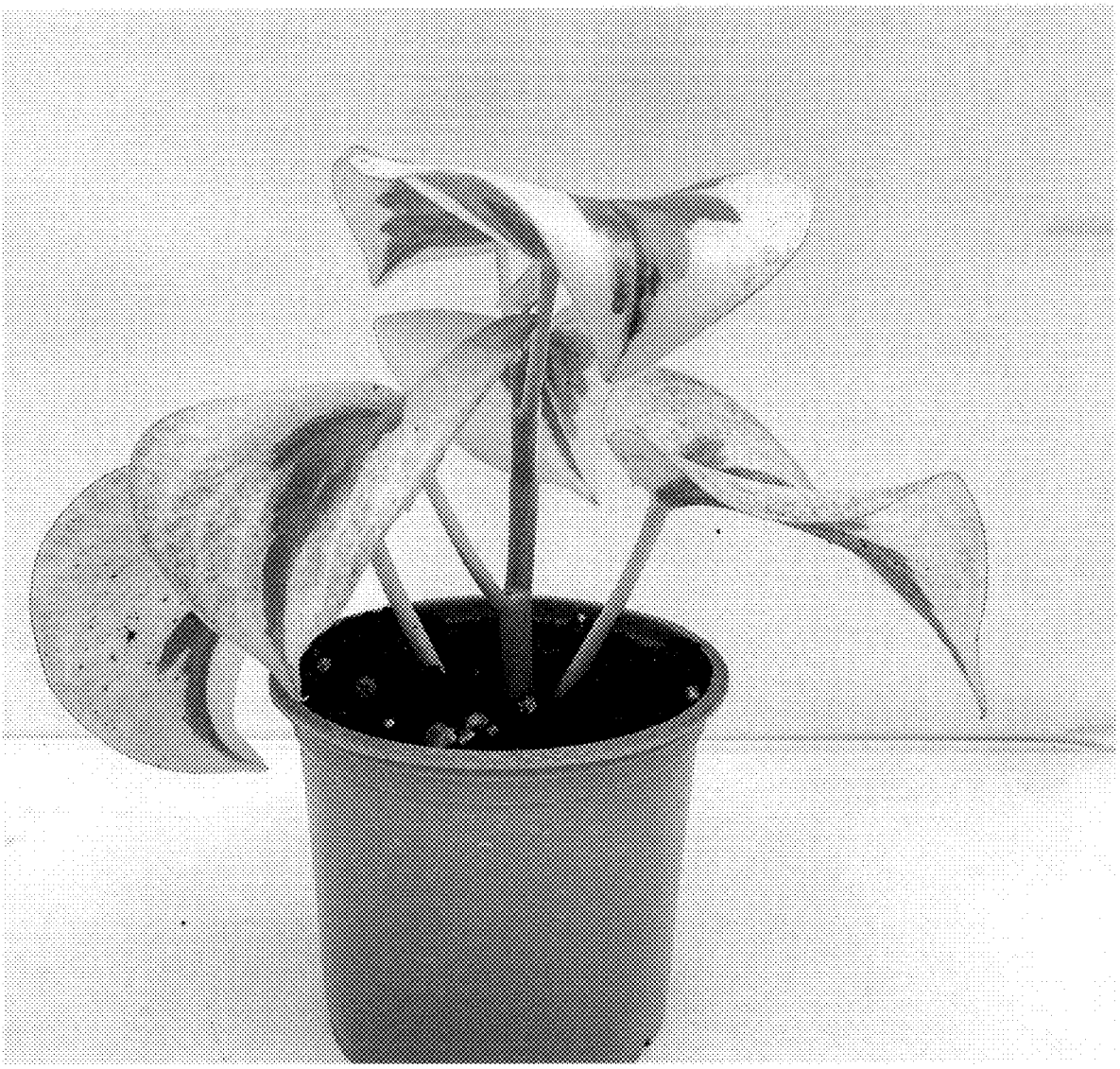
FIG. 4 shows a photo of mature leaves.
Figure 5:
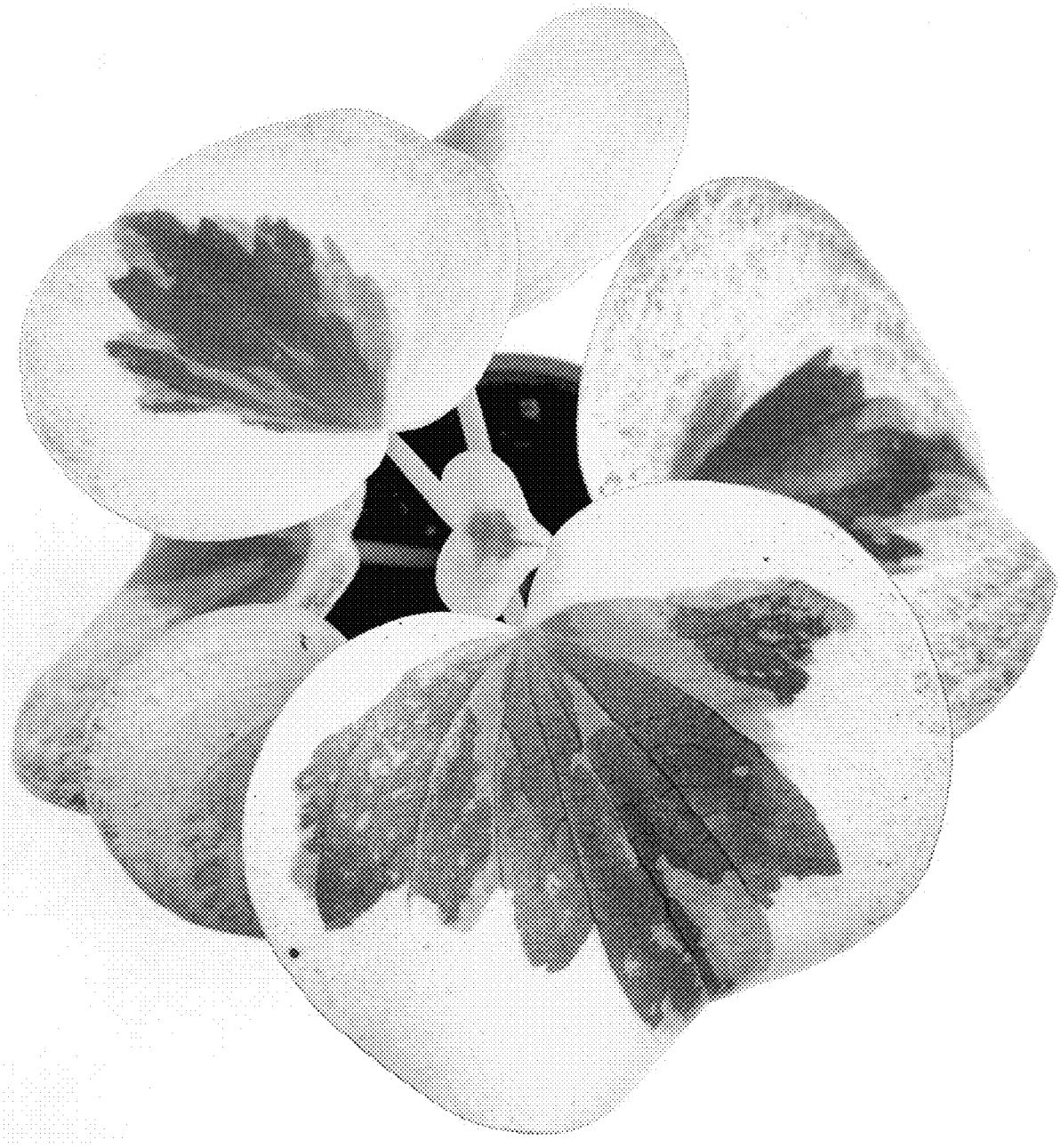
FIG. 5 shows a close-up of a young and mature leaf side by side.

The following is a detailed description of the new *Peperomia* cultivar named 'Verdant Flame'. Data was collected in Nashville, Tenn. from 12 week old plants grown in a glass greenhouse in 10 cm. diameter containers. The time of year was late summer and the temperature range was 18-25 degrees Centigrade during the day, and 18-23 degrees Centigrade at night. The light level was natural light level in the greenhouse between 2-3 pm on a bright sunny day. The age of the plants described is 3 months. No photoperiodic treatments or growth retardants were used. Color determinations are in accordance with The Royal Horticultural Society Colour Chart, except where general color terms of ordinary dictionary significance are used. The growing requirements are similar to the species. 'Verdant Flame' has not been tested under all possible conditions and phenotypic differences may be observed with variations in environmental, climatic, and cultural conditions without any variance in genotype.

Classification:

*Botanical.*—*Peperomia polybotrya.*

*Variety denomination.*—'Verdant Flame'.

*Annual or perennial.*—Ornamental tropical foliage plant.

Parentage: 'Verdant Flame' has been discovered in a cultivation area, not from a cross.

Optimal growth conditions:

*Plant type.*—Potted plant.

*Growth habit.*—Broad upright.

*Plant shape.*—Flattened globe shaped.

*Suitable container size.*—10 cm. pots or larger.

*Plant height.*—20 cm and up.

*Plant width.*—25 cm to 30 cm and up.

*Vigor.*—Moderate to slow growing due to the variegation.

*Low temperature tolerance.*—12 to 14 Centigrade.

*High temperature tolerance.*—26 to 32 Centigrade.

Propagation:

*Type.*—Vegetative, by rooted cuttings in the greenhouse.

*Time to initiate roots* (*summer*).—10 days at 18 to 23 C.

*Time to initiate roots* (*winter*).—12 days at 18 to 23° C.

*Time to produce a rooted cutting.*—Cuttings are placed directly into growing pots. and will take approximately 6 weeks to root.

Plant:

*Growth rate.*—Low to moderate.

*Crop time.*—Approximately 3 to 4 months in Nashville, Tenn.

*Root system.*—Fine and fibrous.

*Plant fragrance.*—None.

*Stem.*—Firm, somewhat flexible.

*Branching habit.*—Main and lateral branches when pinched, occasionally lateral branches occur naturally.

*Number of main branches per plant.*—Average 1.

*Number of lateral branches per plant.*—Average 1, pinching will produce more.

*Main branch dimensions.*—12-18 cm and up in length and 8-12 mm in diameter.

*Internode length.*—2-2.5 cm, depends on growing conditions.

*Stem shape.*—Round.

*Stem luster.*—Slightly glossy, waxy.

*Stem pubescence.*—None.

*Stem angle.*—Average 45-50 degrees.

*Stem strength.*—Firm, yet can snap when bent.

*Stem color* (*young*).—Yellow-Green 145 B to C.

*Stem color* (*mature*).—Yellow-Green 145 C to D.

*Internode color.*—Yellow-Green 145 B to C.

Foliage:

*Leaf arrangement.*—Alternate.

*Compound or single.*—Single.

*Quantity of leaves per branch.*—Average 5-7 and up.

*Leaf shape.*—Cordate.

*Leaf aspect.*—Slightly convex, slightly wavy.

*Leaf apex.*—Cuspidate.

*Leaf base.*—Broad Attenuate.

*Leaf dimensions.*—9-10 cm in length and 8-10 cm and more in width depending on age.

*Texture.*—Thick and smooth (both surfaces).

*Leaf luster.*—Upper surface waxy and moderately glossy, lower surface waxy and slightly glossy.

*Pubescence.*—Absent.

*Leaf margin.*—Entire.

*Venation pattern.*—Pinnate, not very pronounced.

*Young leaf color* (*upper surface*).—The variegation can have 3 or more shades of green. Main color is between Yellow-Green 154 C to D and Yellow-Green 145 B to C. The irregular bands in the center are Green 137 B to C and Greyed-Green 194 A to B. The patches of speckles in between the veins are Green 137 B to C.

*Young leaf color* (*lower surface*).—Yellow-Green 145 C to D and lighter, center Greyed-Green 194 A to B, no speckles.

*Edge between front and back leaf.*—Fine line of Greyed-Purple 185 C to D.

*Mature leaf color* (*upper surface*).—The variegation can have 3 or more shades of green. Main color is between Yellow-Green 154 C to D and Yellow-Green 145 C and lighter, but the leaf is heavily covered in speckles that are Green 137 B to C in between the yellowish veins. The irregular bands in the center are Green 137 B to C and Greyed-Green 194 A to B.

*Mature leaf color* (*lower surface*).—Yellow-Green 145 C to D, center yellow Green 144 A to Yellow-Green 148 C. No speckles.

*Edge between front and back leaf.*—fine line of Greyed-Purple 186 B to C.

*Vein color* (*upper surface*).—Vein color matches the lighter and darker areas of the leaf.

*Vein color* (*lower surface*).—Vein color matches the lighter and darker areas of the leaf.

Petiole:

*Petiole dimensions.*—3-4 mm in diameter, anywhere from 3 cm to 10 cm in length as leaf matures. When mature the diameter is 4-5 mm.

*Petiole texture.*—Glabrous.

*Petiole luster.*—Slightly glossy.

*Petiole pubescence.*—Absent.

*Petiole strength.*—Fairly strong and flexible.

*Petiole color.*—Yellow-Green 145 C.

*Flower.*—'Verdant Flame' has produced the typical *Peperomia polybotrya* peduncle with 1-5 elongated thin, white rubbery flowers.

*Peduncle.*—3 mm with a waxy smooth texture and 5-7 length, and Yellow-Green 146 C to D with occasional touches of Greyed-Purple 186 B.

*Pedicel.*—2.5 mm in diameter waxy smooth texture and 1-4 cm in length. Inflorescence with flower is 10-15 cm in length and it is spicate, spike which lasts between 2-3 weeks, with average of 3 flowers.

*Inflorescence.*—4-7 cm in length, between Yellow-Green 4 D and White Group 155A.

*Fruit and seed.*—'Verdant Flame' has not produced fruit or seed to date.

Weather resistance: Mildly drought tolerant.

Disease/pest resistance: High resistance to most.

Disease/pest susceptibility: Not observed so far.

I claim:

1. A new and distinct variety of *Peperomia* plant named 'Verdant Flame', substantially as illustrated, and described herein.

* * * * *